US00RE39576E

(19) United States
(12) Reissued Patent
Hodson et al.

(10) Patent Number: US RE39,576 E
(45) Date of Reissued Patent: Apr. 17, 2007

(54) ENZYME INHIBITORS

(75) Inventors: Harold Francis Hodson, Beckenham (GB); Richard Michael John Palmer, Hayes (GB); David Alan Sawyer, Beckenham (GB); Richard Graham Knowles, Stevenage (GB); Karl Witold Franzmann, London (GB); Martin James Drysdale, Stevenage (GB); Patricia Ifeyinwa Davies, London (GB); Helen Alice Rebecca Clark, Purley (GB); Barry George Shearer, Cary, NC (US); Steven Smith, Stevenage (GB)

(73) Assignee: Smithkline Beecham Corporation, Philadelphia, PA (US)

(21) Appl. No.: 10/407,204

(22) PCT Filed: Jun. 14, 1995

(86) PCT No.: PCT/GB95/01378

§ 371 (c)(1),
(2), (4) Date: Dec. 27, 1996

(87) PCT Pub. No.: WO95/34534

PCT Pub. Date: Dec. 21, 1995

Related U.S. Patent Documents

Reissue of:
(64) Patent No.: 5,889,056
Issued: Mar. 30, 1999
Appl. No.: 08/750,679
Filed: Dec. 27, 1996

(30) Foreign Application Priority Data

Jun. 15, 1994 (EP) ..... 94304314
May 15, 1995 (GB) ..... 9509774

(51) Int. Cl.
*A61K 31/195* (2006.01)

(52) U.S. Cl. ..... 514/562; 514/550; 560/150; 562/556

(58) Field of Classification Search ..... 514/562, 514/560; 560/150; 562/556
See application file for complete search history.

(56) References Cited

FOREIGN PATENT DOCUMENTS

| | | | |
|---|---|---|---|
| DE | C 830 640 | | 1/1952 |
| DE | A 43 10 202 | | 10/1993 |
| EP | A 0 200 051 | | 12/1986 |
| FR | 2 727 111 | * | 5/1996 |
| WO | WO A 93 13055 | | 7/1993 |

OTHER PUBLICATIONS

Tanaka et al, J. Biol. Chem. 249 (16) 5285–9 (1974).
'Houben–Weyl "Methoden der organischen Chemie", Bd E5', 1985, George Thieme Vergag, Stuttgart.
Chemcial Abstracts, vol. 72, No. 13, Mar. 30, 1970, Abstract No. 67238p, Hermann, Peter et al, 'Synthesis of some sulfur–containing amino acid analogs', p. 438; col. 1 & J. Prakt. Chem., vol. 311, No. 6, 1969, pp. 1018–1028.
Chemical Abstracts, vol. 66, No. 21, May 22, 1967, Columbus, Ohio, Abstract No. 91926h, Donald T. Elmore et al, 'Kinetics and mechanism of catalysis by proteolytic enzymes . . . ', p. 8590; col. 1; see abstract & Biochem J., vol. 102, 1967, pp. 728–734.

* cited by examiner

*Primary Examiner*—Samuel Barts
(74) *Attorney, Agent, or Firm*—Nixon & Vanderhye P.C.

(57) ABSTRACT

A compound of formula (I)

(I)

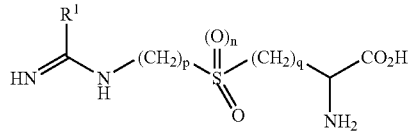

wherein $R^1$ is a $C_{1-6}$ straight or branched chain alkyl group, a $C_{2-6}$alkenyl group, a $C_{2-6}$ alkynyl group, a $C_{3-6}$cycloalkyl group or a $C_{3-6}$cycloalkyl$C_{1-6}$alkyl group, each optionally substituted by one to three groups independently selected from: —CN; —$NO_2$; a group —$COR^2$ wherein $R^2$ is hydrogen, $C_{1-6}$ alkyl, —$OR^3$ wherein $R^3$ is hydrogen or $C_{1-6}$alkyl or $NR^4R^5$ wherein $R^4$ and $R^5$ are independently selected from hydrogen or $C_{1-6}$ alkyl; a group —$S(O)_mR^6$ wherein m is 0, 1 or 2, $R^6$ is hydrogen, $C_{1-6}$ alkyl, hydroxy or $NR^7R^8$ wherein $R^7$ and $R^8$ are independently hydrogen or $C_{1-6}$ alkyl; a group $PO(OR^9)_2$ wherein $R^9$ is hydrogen or $C_{1-6}$ alkyl; a group $NR^{10}R^{11}$ wherein $R^{10}$ and $R^{11}$ are independently selected from hydrogen, $C_{1-6}$ alkyl, —$COR^{12}$ wherein $R^{12}$ is hydrogen or $C_{1-6}$ alkyl, or —$S(O)_{m'}R^{13}$ wherein m' is 0, 1 or 2 and $R^{13}$ is hydrogen or $C_{1-6}$ alkyl; halo; or a group —$OR^{14}$ wherein $R^{14}$ is hydrogen, $C_{1-6}$ alkyl optionally substituted by one to three halo atoms, $C_{6-10}$ aryl or —$COR^{15}$ wherein $R^{15}$ is hydrogen or $C_{1-6}$ alkyl; p is 2 or 3, q is 1 or 2 and n is 0 or 1 and all salts, esters, amides and physiologically acceptable prodrugs thereof; pharmaceutical uses and formulations therefor; and processes for their preparation are disclosed.

7 Claims, No Drawings

ENZYME INHIBITORS

Matter enclosed in heavy brackets [ ] appears in the original patent but forms no part of this reissue specification; matter printed in italics indicates the additions made by reissue.

This application is a 371 of PCT/GB95/01378 filed Jun. 14, 1995.

The present invention relates to amidino sulphoxide and sulphone derivatives, to methods for their manufacture, to pharmaceutical compositions containing them and to their use in therapy, in particular their use as selective inhibitors of inducible nitric oxide synthase.

It has been known since the early 1980's that the vascular relaxation brought about by acetylcholine is dependent on the presence of the endothelium and this activity was ascribed to a labile humoral factor termed endothelium-derived relaxing factor (EDRF). The activity of glyceryl trinitrate as a vasodilator has been known for well over 100 years and it is now known that NO is the active component of amylnitrite, glyceryltrinitrite and other nitrovasodilators. The recent identification of EDRF as NO has coincided with the discovery of a biochemical pathway by which NO is synthesized from the amino acid L-arginine by the enzyme NO synthase.

NO is the endogenous stimulator of the soluble guanylate cyclase enzyme and is involved in a number of biological actions in addition to endothelium-dependent relaxation including cytotoxicity of phagocytic cells and cell-to-cell communication in the central nervous system (see Moncada et al, Biochemical Pharmacology, 38, 1709–1715 (1989) and Moncada et al, Pharmacological Reviews, 43, 109–142 (1991)). It is now thought that excess NO production may be involved in a number of conditions, including conditions which involve systemic hypotension such as septic shock and therapy with certain cytokines, and many inflammatory diseases such as arthritis.

The synthesis of NO from L-arginine can be inhibited by the L-arginine analogue, $N^G$-monomethyl-L-arginine (L-NMMA), and the therapeutic use of L-NMMA for the treatment of septic (toxic) shock and other types of systemic hypotension has been proposed (WO 91/04024) and GB-A-2240041). The therapeutic use of certain other NO synthase inhibitors apart from L-NMMA for the same purpose has also been proposed in WO 91/04024 and in EP-A-0446699.

It has recently become apparent that there are at least three isoenzymes of NO synthase (reviewed in Knowles and Moncada, Biochem. J. (1994) 298, 249–258) as follows:

(i) a constitutive, $Ca^{++}$/calmodulin dependent enzyme (eNOS) which is present in vascular endothelial cells, and that releases NO in response to receptor or physical stimulation.

(ii) a constitutive, $Ca^{++}$/calmodulin dependent enzyme (nNOS), located in the brain and some peripheral nervous systems, that releases NO in response to receptor or physical stimulation.

(iii) a $Ca^{++}$ independent enzyme (iNOS) which is induced after activation of vascular smooth muscle, macrophages, endothelial cells, and a number of other cells by endotoxin and cytokines. Once expressed this inducible NO synthase synthesises NO for long periods.

The NO released by eNOS and nNOS acts as a transduction mechanism underlying several physiological responses. The NO produced by iNOS acts as a cytotoxic molecule for invading microorganisms. It also appears that the adverse effects of excess NO production, in particular pathological vasodilation, vascular leakage and tissue damage, may result largely from the effects of NO synthesized by iNOS.

The NO synthase inhibitors proposed for therapeutic use so far, such as L-NMMA and nitroarginine, are non-selective in that they inhibit all the NO synthase isoenzymes. Use of such a non-selective NO synthase inhibitor requires that great care is taken in order to avoid the potentially serious consequences of over-inhibition of the eNOS including hypertension and possible thrombosis and tissue damage. In particular, in the case of the therapeutic use of L-NMMA for the treatment of septic and/or toxic shock it has been recommended that the patient must be subject to continuous blood pressure monitoring throughout the treatment. Thus, whilst non-selective NO synthase inhibitors have therapeutic utility provided that appropriate precautions are taken, NO synthase inhibitors which are selective in the sense that they inhibit iNOS to a considerably greater extent than eNOS would be of even greater therapeutic benefit and much easier to use.

Patent application PCT/GB9202387 discloses a group of amidino derivatives of the formula (0)

(O)

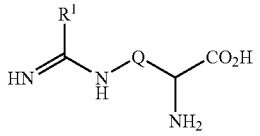

and salts, and pharmaceutically acceptable esters and amides thereof, in which:

$R^1$ is a $C_{1-6}$ straight or branched chain alkyl group, a $C_{2-6}$ alkenyl group, a $C_{2-6}$ alkynyl group, a $C_{3-6}$cycloalkyl group or a $C_{3-6}$cycloalkyl $C_{1-6}$alkyl group;

Q is an alkylene, alkenylene or alkynylene group having 3 to 6 carbon atoms and which may optionally be substituted by one or more $C_{1-3}$alkyl groups; or Q is a group of formula —$(CH_2)_pX(CH_2)_q$— where p is 2 or 3, q is 1 or 2 and X is $S(O)_x$, where x is 0, 1 or 2, O or $NR^2$ where $R^2$ is H or $C_{1-6}$alkyl; or Q is a group of formula —$(CH_2)_rA(CH_2)_s$— where r is 0, 1 or 2, s is 0, 1 or 2 and A is a 3 to 6 membered carbocyclic or heterocyclic ring which may optionally be substituted by one or more suitable substituents such as $C_{1-6}$alkyl, $C_{1-6}$alkoxy, hydroxy, halo, nitro, cyano, trifluoro$C_{1-6}$ alkyl, amino, $C_{1-6}$alkylamino or di$C_{1-6}$alkylamino which have activity as inhibitors of the NO synthase enzyme.

The present inventors have found a particular group of compounds which are selective inhibitors of iNOS, having little or no effect on eNOS. Accordingly the present invention provides compounds of formula (I)

(I)

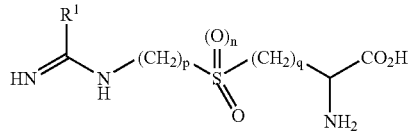

wherein $R^1$ is a $C_{1-6}$ straight or branched chain alkyl group, a $C_{2-6}$alkenyl group, a $C_{2-6}$ alkynyl group, a $C_{3-6}$cycloalkyl group or a $C_{3-6}$cycloalkyl$C_{1-6}$alkyl group, each optionallly substituted by one to three groups independently selected from; halo; —CN; —$NO_2$; a group —$COR^2$ wherein $R^2$ is hydrogen, $C_{1-6}$ alkyl, —$OR^3$ wherein $R^3$ is hydrogen or $C_{1-6}$ alkyl, or $NR^4R^5$ where $R^4$ and $R^5$ are independently selected from hydrogen or $C_{1-6}$ alkyl; a group —$S(O)_mR^6$ wherein m is 0, 1 or 2, $R^6$ is hydrogen, $C_{1-6}$ alkyl, hydroxy or $NR^7R^8$ wherein $R^7$ and $R^8$ are independently hydrogen or $C_{1-6}$ alkyl; a group $PO(OR^9)_2$ wherein $R^9$ is hydrogen or $C_{1-6}$ alkyl; a group $NR^{10}R^{11}$ wherein $R^{10}$ and $R^{11}$ are independently selected from hydrogen, $C_{1-6}$ alkyl, —$COR^{12}$ wherein $R^{12}$ is hydrogen or $C_{1-6}$ alkyl, or —$S(O)_mR^{13}$ wherein m' is 0, 1 or 2 and $R^{13}$ is hydrogen or $C_{1-6}$ alkyl; or a group —$OR^{14}$ wherein $R^{14}$ is hydrogen, $C_{1-6}$ alkyl optionally substituted by one to three halo atoms, $C_{6-10}$ aryl or —$COR^{15}$ wherein $R^{15}$ is hydrogen or $C_{1-6}$ alkyl;

p is 2 or 3, q is 1 or 2 and n is 0 or 1 and all salts, esters, amides and physiologically acceptable prodrugs thereof.

Suitably $R^1$ is $C_{1-6}$ alkyl, $C_{2-6}$ alkenyl or alkynyl or $C_{3-6}$ cycloalkyl each group being optionally substituted by one to three groups independently selected from —CN; —$NO_2$; a group —$COR^{2a}$ wherein $R^{2a}$ is hydrogen, $C_{1-4}$ alkyl, hydroxy or amino; a group —$S(O)_mR^{6a}$ wherein m is as hereinbefore defined and $R^{6a}$ is hydrogen, $C_{1-4}$ alkyl, hydroxy or amino; a group —$PO(OR^{9a})_2$ wherein $R^{9a}$ is hydrogen or $C_{1-4}$ alkyl; a group $NR^{10a}R^{11a}$ wherein $R^{10a}$ and $R^{11a}$ are independently selected from hydrogen, $C_{1-4}$ alkyl, —$COR^{12a}$ or $S(O)mR^{13a}$ wherein m' is as hereinbefore defined and $R^{12a}$ and $R^{13a}$ are independently hydrogen or $C_{1-4}$ alkyl; a group $OR^{14a}$ wherein $R^{14a}$ is hydrogen, $C_{1-4}$ alkyl optionally substituted by one to three halo atoms, phenyl, benzyl or —$COR^{15a}$ wherein $R^{15a}$ is hydrogen or $C_{1-4}$ alkyl.

Preferably, $R^1$ is a $C_{1-4}$ alkyl group or a $C_{2-4}$ alkenyl or alkynyl group, optionally substituted by one to three groups independently selected from —CN; a group —$COR^2$ wherein $R^2$ is as hereinbefore defined, a group —$S(O)_mR^6$ wherein m and $R^6$ are as hereinbefore defined; a group $NR^{10}R^{11}$ wherein $R^{10}$ and $R^{11}$ are as hereinbefore defined; halo; or a group —$OR^{14}$ wherein $R^{14}$ is as hereinbefore defined.

Most preferably $R^1$ is a methyl or ethyl group optionally substituted by one to three substituents independently selected from halo, a group —$OR^{14}$ wherein $R^{14}$ is as hereinbefore defined or $S(O)_mR^6$ wherein m and $R^6$ are as hereinbefore defined.

A preferred group of compounds are those of formula (IA)

(IA)

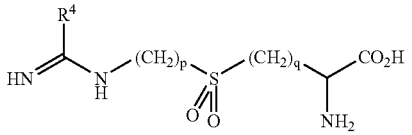

wherein $R^1$, $R^2$, p and q are as hereinbefore defined.

Preferably $R^1$ is unsubstituted or is substituted by only one group.

Preferred compounds include:

2-Amino-6-(1-iminoethylamino)4,4-dioxo4-thiahexanoic acid

2-Amino-6-(1-iminoethylamino)4-oxo4-thiahexanoic acid

2-Amino-7-(1-iminoethylamino)-5-oxo-5-thiaheptanoic acid

2-Amino-7-(1-iminoethylamino)-5,5-dioxo-5-thiaheptanoic acid

2-Amino-6-(1-imino-2-fluoroethylamino)-4,4-dioxo-4-thiahexanoic acid

2-Amino-6-(1-imino-2-methoxyethylamino)-4,4-dioxo-4-thiahexanoic acid

2-Amino-6-(2-acetoxy-1-iminoethylamino)-4,4-dioxo-4-thiahexanoic acid

2-Amino-6-(2-benzyloxy-1-iminoethylamino)-4,4-dioxo-4-thiahexanoic acid

2-Amino-6-(2-methylthio-1-iminoethylamino)-4,4-dioxo-4-thiahexanoic acid

2-Amino-6-(2-hydroxy-1-iminoethylamino)-4,4-dioxo-4-thiahexanoic acid and all salts, ester, amides and physiologically acceptable prodrugs thereof.

Particularly preferred are 2-Amino-6-(1-iminoethylamino)-4,4-dioxo-4-thiahexanoic acid and 2-Amino-6-(1-imino-2-fluoroethylamino)-4,4-dioxo-4-thiahexanoic acid. Preferably the compounds are in the R configuration.

The compounds of formula (I) may include a number of asymmetric centers in the molecule depending on the precise meaning of the various groups and formula (I) is intended to include all possible isomers. The compounds of formula (I) all include an asymmetric center in the

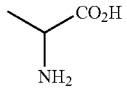

group and although the natural L or (S) chirality of arginine is preferred, it is again intended that the formula should include all possible isomers, either individually or admixed in any proportions.

One embodiment of the present invention provides a compound of formula (IB)

(IB)

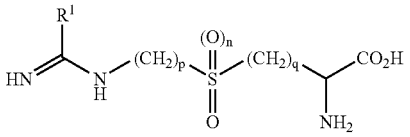

and salts, and pharmaceutically acceptable esters and amides thereof in which $R^1$ is a $C_{1-6}$ straight or branched chain alkyl group, a $C_{2-6}$alkenyl group, a $C_{2-6}$ alkynyl group, a $C_{3-6}$cycloalkyl group or a $C_{3-6}$cycloalkyl$C_{1-6}$alkyl group; p is 2 or 3, q is 1 or 2 and n is 0 or 1.

Another embodiment of the present invention provides a compound of formula (IC)

(IC)

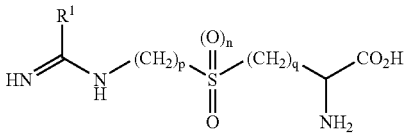

wherein n is 0 or 1; p is 2 or 3; q is 1 or 2; $R^1$ is a $C_{1-6}$ straight or branched chain alkyl group, a $C_{2-6}$ alkenyl group, a $C_{2-6}$ alkynyl group, a $C_{3-6}$ cycloalkyl group or a $C_{3-6}$ cycloalkyl $C_{1-6}$ alkyl group each substituted by one to three groups independently selected from: —CN; —$NO_2$; a group —$COR^2$ wherein $R^2$ is hydrogen, $C_{1-6}$ alkyl, —$OR^3$ wherein $R^3$ is hydrogen or $C_{1-6}$ alkyl, or $NR^4R^5$ wherein $R^4$ and $R^5$ are independently selected from hydrogen or $C_{1-6}$ alkyl; a group —$S(O)_mR^6$ wherein m is 0, 1 or 2, $R^6$ is hydrogen, $C_{1-6}$ alkyl, hydroxy or $NR^7R^8$ wherein $R^7$ and $R^8$ are independently hydrogen or $C_{1-6}$ alkyl; a group $PO(OR^9)_2$ wherein $R^9$ is hydrogen or $C_{1-6}$ alkyl; a group $NR^{10}R^{11}$ wherein $R^{10}$ and $R^{11}$ are independently selected from hydrogen, $C_{1-6}$ alkyl, —$COR^{12}$ wherein $R^{12}$ is hydrogen or $C_{1-6}$ alkyl, or —$S(O)_{m'}R^{13}$ wherein m' is 0, 1 or 2 and $R^{13}$ is hydrogen or $C_{1-6}$ alkyl; halo; or a group —$OR^{14}$ wherein $R^{14}$ is hydrogen, $C_{1-6}$ alkyl optionally substituted by one to three halo atoms, $C_{6-10}$ aryl or —$COR^{15}$ wherein $R^{15}$ is hydrogen or $C_{1-6}$ alkyl; and all salts, esters, amides and physiologically acceptable prodrugs thereof.

The term "halo" means fluoro, chloro, bromo, or iodo, and preferably fluoro.

Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, trifluoroacetic, succinic, oxalic, fumaric, maleic, oxaloacetic, methanesulphonic, ethanesulphonic, ρ-toluenesulphonic, benzenesulphonic and isethionic acids. Salts of the compounds of formula (I) can be made by reacting the appropriate compound in the form of the free base with the appropriate acid.

Pharmaceutically acceptable esters and amides of the compounds of formula (I) may have the acid group replaced by —$CO_2R^3$ where $R^3$ is for example $C_{1-6}$alkyl, aryl or aryl$C_{1-3}$alkyl or —$COR^4$ where $R^4$ is the residue of a suitable natural or synthetic amino acid.

By the term physiologically acceptable prodrug is meant derivatives of compounds of formula (I) which have the same physiological function as the free compound of formula (I), for example, by being convertible in the body thereto. Such prodrugs may or may not have activity in their own right.

A further aspect of the present invention also provides compounds of formula (I) as hereinbefore defined and all salts, esters, amides and physiologically acceptable prodrugs thereof, for use in medicine, in particular the treatment of conditions where there is an advantage in inhibiting NO production from L-arginine by the action of NO synthase and more specifically of conditions where there is an advantage in inhibiting NO production by the iNOS isoenzyme over production by eNOS.

According to a further aspect, the present invention provides the use of a compound of formula (I) and all salts, estersm amides and physiologically acceptable prodrugs thereof, in the manufacture of a medicament for the treatment of a condition where there is an advantage in inhibiting NO production from arginine by the action of NO synthase and, more specifically, by the action of iNOS.

In a further aspect, there is provided the use of a compound of formula (I) or a salt, ester, amide or physiologically acceptable prodrug thereof in the manufacture of a medicament for the treatment of shock states resulting from overproduction of NO by iNOS such as septic shock, or shock caused by fulminant hepatic failure or by therapy with cytokines such as TNF, IL-1 and IL-2 or therapy with cytokine-inducing agents, for example 5,6-dimethylxanthenone acetic acid.

A further aspect of the present invention provides the use of a compound of formula (I) or a salt, ester, amide or physiologically acceptable prodrug thereof in the manufacture of a medicament for the treatment of an inflammatory condition, such as arthritis.

In the alternative there is provided a method for the treatment of a condition where there is an advantage in inhibiting NO production from L-arginine by the action of NO synthase, and in particular by iNOS, comprising administering to a mammal in need thereof a pharmaceutically effective amount of a compound of formula (I) as hereinbefore defined or a salt, ester, amide or physiologically acceptable prodrug thereof.

Other conditions where there is an advantage in selectively inhibiting iNOS include a wide range of auto-immune and/or inflammatory diseases, such as those of the joint (e.g. rheumatoid arthritis, osteoarthritis), of the gastrointestinal tract (e.g. ulcerative colitis and other inflammatory bowel diseases, gastritis and mucosal inflammation resulting from infection, the enteropathy provoked by non-steroidal anti-inflammatory drugs), of the lung (adult respiratory distress syndrome, asthma), of the heart (myocarditis), of the nervous tissue (e.g. multiple sclerosis), of the pancreas (e.g. diabetes melitus), of the kidney (e.g. glomerulonephritis), of the skin (e.g. dermatitis, psoriasis, urticaria) as well as of transplanted organs (rejection) and multi-organ diseases (e.g. systemic lupus erythematosis). Furthermore there is evidence for overproduction of NO by iNOS in atherosclerosis. Therefore, a yet further aspect of the present invention provides the use of a compound of formula (I) or a salt, ester, amide of physiologically acceptable prodrug thereof in the manufacture of a medicament for use in treating the above conditions.

Inhibition of nNOS and/or iNOS is of benefit in the treatment of diseases of the nervous system due to over production of NO by this isoenzyme, particularly the treatment of cerebral ischemia. Other diseases include CNS trauma, epilepsy, AIDS dementia, chronic neurodegenerative disease and chronic pain, and conditions in which non-adrenegic non-cholinergic nerve may be implicated such as priapism, obesity and hyperphagia. Accordingly the present invention also provides the use of a compound of formula (I) or a salt, ester, amide or physiologically acceptable prodrug thereof thereof in the manufacture of a medicament for use in treating the above conditions.

Furthermore inhibition of NO synthase may be of advantage in preventing the lymphocyte loss associated with HIV infection, in increasing the radiosensitivity of tumours during radiotherapy and in reducing tumour growth and metastasis.

Inhibition of both iNOS and nNOS may be of benefit in the treatment of certain conditions where both isoenzymes play a role, for example CNS conditions such as cerebral ischemia.

As used herein, reference to "treatment" of a patient is intended to include prophylaxis; the term "mammal" is intended to include a human or an animal.

The activity of compounds of formula (I) and all salts, esters, amides and physiologically acceptable prodrugs thereof as NO synthase inhibitors can be determined using isolated human or rodent enzymes, the rat aortic ring or in vivo in mice according to the methods described hereinafter.

Whilst it may be possible for the compounds of formula (I) and all salts, esters, amides and physiologically acceptable prodrugs thereof to be administered as the raw chemical, it is preferable to present them as a pharmaceutical formulation. According to a further aspect, the present invention provides a pharmaceutical formulation comprising a compound of formula (I) and all salts, esters, amides and physiologically acceptable prodrugs thereof, together with one or more pharmaceutically acceptable carriers therefor and optionally one or more other therapeutic ingredients.

The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) and all salts, esters, amides and physiologically acceptable prodrugs thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention may be administered orally or via injection at a dose of from 0.1 to 1500 mg/kg per day, preferably 0.1 to 500 mg/kg per day. The dose range for adult humans is generally from 5 mg to 35 g/day and preferably 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of the present invention may be administered in combination with one or more other active ingredients. Such other active ingredients suitable for concurrent administration will be clear to a physician, but could be for example an anti-inflammatory agent such as a corticosteroid, e.g methylprednisolone. Compounds of formula (I) are competitive inhibitors with respect to L-arginine and therefore it may not be appropriate of course to concurrently treat patients with preparations (e.g. total parenteral nutrition) which have a high L-arginine content.

The compounds of formula (I) and all salts, esters, amides and physiologically acceptable prodrugs thereof are preferably administered orally or by injection (intravenous or subcutaneous). The precise amount of compound administered to a patient will be the responsibility of the attendant physician. However the dose employed will depend on a number of factors, including the age and sex of the patient, the precise disorder being treated, and its severity. Also the route of administration may vary depending on the condition and its severity.

Compounds of formula (I) are novel and accordingly a further aspect of the present invention provides a process for the preparation thereof.

Compounds of formula (I) can be prepared:

(a) by the oxidation of a compound of the formula (II):

(II)

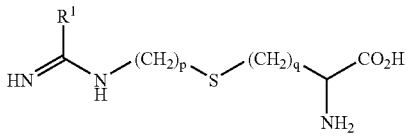

The oxidation may be carried out by methods known in the art, for example by treatment with an oxygen-rich compound, such as 30% hydrogen peroxide and 0.5M ammonium molybdate in perchloric acid.

Compounds of the formula (II) may be prepared by the reaction of an amino acid of formula (III)

(III)

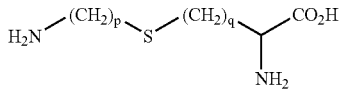

or a protected derivative thereof, with a compound of formula (IV)

(IV)

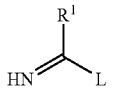

where L is a leaving group and $R^1$, p and q are as defined hereinbefore, followed by removal of any protecting groups present, to give a compound of formula (II).

Suitable leaving groups L include —$OR^5$ and —$SR^5$ where $R^5$ is a lower alkyl group, e.g. $C_{1-4}$alkyl, preferably methyl or ethyl.

The compound of formula (III) will generally be used in a form in which the amino acid functionality is protected by suitable protecting groups and in this connection reference can be made to T. W. Greene and P. G. M. Wuts, Protective Groups in Organic Synthesis, 2nd Edition, John Wiley and Sons Inc., 1991. The protecting groups can then be removed in conventional manner (loc. cit.) as the final stage of the process to yield the compound of formula (II). For example the amino acid functionality can be protected as the copper salt with deprotection taking place on an ion exchange column which is employed to remove inorganic ions from the reaction mixture.

The compounds of formula (IV) can be used in the form of the free base or as an acid addition salt, e.g. the hydrochloride or hydroiodide salt.

The reaction is generally carried out in a suitable solvent in the presence of base, e.g. an alkali metal hydroxide such as sodium hydroxide, preferably at a pH of about 9 to 11 and generally at a temperature from 0° C. up to the reflux temperature of the solvent, preferably 0° C. to 50° C. The preferred solvent is water although the reaction may also be carried out in a polar solvent such as a lower alcohol, e.g. methanol or ethanol, or an amide, e.g. dimethylformamide, either alone or in admixture with water, and this may be advantageous in certain circumstances.

The compounds of formula (III) are in general known compounds which can be converted into appropriate protected derivatives in known manner. The imidates and thioimidates of formula (IV) (L is —$OR^5$ and —$SR^5$ respectively) are also in general known compounds and the reaction of such compounds with a primary amine is discussed for example in The Chemistry of Amidines and imidates, Vol. 2, Eds. Saul Patai and Zvi Rappaport, John Wiley and Sons Inc., 1991.

(b) by the deprotection of a compound of formula (V)

(V)

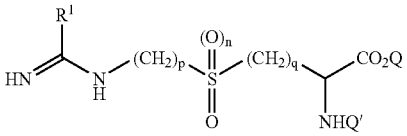

wherein $R^1$, n, p and q are as hereinbefore defined, Q is hydrogen or a carboxyl protecting group and Q' is a protecting group, optionally followed by conversion into another compound of formula (I). Examples of suitable protecting groups include tertbutoxycarbonyl, benzyloxycarbonyl, alkyl, tert-butyl, benzyl etc. Other suitable groups which may be used will be known to one of ordinary skill in the art. When the protecting group is acid labile, for example as in the case of Q being alkyl, the reaction may be carried out by acid hydrolysis, for example by reaction with hydrogen chloride in dioxane, HBr/acetic acid is glacial acetic acid or trifluoroacetic acid in dichloromethane, at a non-extreme temperature of from −5° C. to 100° C., preferably room temperature. When the protecting group is cleavable by hydrogenolysis, for example benzyloxycarbonyl, the deprotection may be carried out using hydrogen over a catalyst, for example palladium/charcoal.

Compounds of formula (V) may be prepared by the reaction of a compound of formula (VI)

(VI)

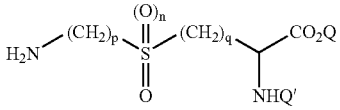

wherein n, p, q, Q and Q' are as hereinbefore defined, with a compound of formula (VII)

(VII)

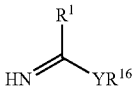

wherein $R^1$ is as hereinbefore defined, Y is O or S and $R^{16}$ is $C_{1-6}$ alkyl, phenyl-$C_{1-6}$-alkyl, or naphthyl-$C_{1-6}$-alkyl for example benzyl. The reaction may suitably be carried out in a polar solvent, for example a $C_{1-6}$ alcohol such as methanol or ethanol, at a non-extreme temperature of from −50° C. to 150° C., for example −5° C. to 50° C. such as room temperature.

Intermediates of formula (VI) and derivatives thereof wherein the free amino group is protected are novel and accordingly provide a further aspect of the present invention. A particularly preferred intermediate is t-butyl-6-benzyloxycarbonyl amino-2-t-butoxycarbonylamino-4,4-dioxo-4-thiahexanoate.

Certain compounds of formula (VII) wherein Y is S are novel, and may be prepared as hereinafter described.

Compounds of formula (VI) may be prepared by the oxidation of a compound of formula (VIII)

(VIII)

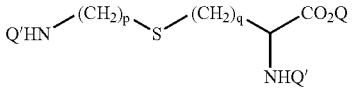

wherein p, q, Q and Q' are as hereinbefore defined, and Q" is a suitable protecting group, for example benzyloxycarbonyl, followed by removal of the protecting group Q". The oxidation reaction may be carried out by standard methods known in the art, for example according to the method described in Tet. Lett. (1981) 22 (14), 1287, or by reaction with m-chloroperbenzoic acid to give the sulphoxide product, followed by reaction with "Oxone" if the sulphone product is required. The reaction is suitably carried out in a polar solvent, for example water or a lower alcohol, such as ethanol, or a mixture thereof.

Removal of the protecting group may be effected by standards methods known to one skilled in the art, for example with catalytic transfer hydrogenation conditions using, for example, formic acid in alcohol, such as methanol, in the presence of a suitable catalyst, such as 10% palladium on charcoal.

Compounds of formula (VIII) may be prepared by the reaction of (i) a compound of formula

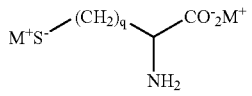

(IX)

wherein q is hereinbefore defined and $M^+$ is a suitable cation eg. $Na^+$, with a compound of formula (X)

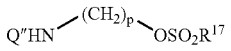

(X)

wherein p and Q" are as hereinbefore defined, and $R^{17}$ is a $C_{1-6}$ alkyl group or an aryl group, followed by protection of the carboxy and amino groups with protecting groups Q and Q', or vice versa.

Compounds of formula (IX) are not normally isolated and may be prepared by reductive cleavage of a compound of formula (XI):

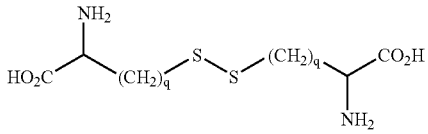

(XI)

wherein q is as hereinbefore defined.

The cleavage may be carried out by methods known in the art, eg by the use of sodium in liquid ammonia at a temperature of from −78° C. to 0° C., and preferably around −40° C.

Compounds of formula (IX) may also be formed by the treatment of a compound of formula (XII)

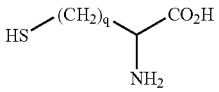

(XII)

with a suitable inorganic base, eg sodium hydrogen carbonate. The reaction is carried out in a suitable solvent, eg DMF.

(ii) By the reaction of a compound of formula (XII) as hereinbefore defined with a suitable organic base eg DBU. The reaction is carried out in a suitable solvent eg toluene at a non-extreme temperature of from 0° to 100° C., preferably room temperature.

Compounds of formula (X), (XI) and (XII) are commercially available or may be prepared by methods readily known to one skilled in the art.

Most intermediates of formula (VII) wherein Y is S are novel. Accordingly the present invention further provides an intermediate of formula (VII')

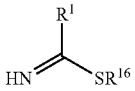

(VII')

wherein $R^1$ and $R^{16}$ are as hereinbefore defined, and a process for the preparation thereof with the proviso that:

(a) the compound of formula (VII') is not 2,2-dichlorothiopropionimidic, benzyl ester; and (b) $R^1$ is not $C_{1-5}$ alkyl, cyclopropyl or cyclohexyl.

Preferred intermediates include:

S-benzyl-2-methoxythioacetimidate

S-benzyl-2-fluorothioacetimidate

S-(2-naphthylmethyl)-2,2-difluorothioacetimidate

S-(2-naphthylmethyl)-2-thiomethylthioacetimidate

Intermediates of formula (VII') may by prepared by the reaction of a compound of formula (XIII)

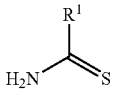

(XIII)

with a reagent of formula $R^{16}L'$, suitably $PhCH_2L'$, wherein $R^{16}$ is as hereinbefore defined and L' is a suitable leaving group, for example a halo atom such as chloro.

Compounds of formula (XIII) are commercially available or may be prepared by methods known to one skilled in the art.

The present invention will now be illustrated by the following examples:

Intermediate A

Preparation of t-Butyl-6-amino-2-t-butoxycarbonylamino-4,4-dioxo-4-thiahexanoate formate salt t-Butyl-6-benzyloxycarbonylamino-2-t-butoxycarbonylamino-4,4-dioxo-4-thiahexanoate 152 mg) dissolved in 5% formic acid/methanol (8 ml) was added dropwise to a stirred suspension of 10% Pd/C in 5% formic acid/methanol (2 ml) at 0° C. The reaction mixture was stirred at 0° C. for 1 h then at room temperature for 1–2 h. The reaction mixture was filtered through hyflo, and the catalyst washed with methanol (25 ml) and water (25 ml). The filtrate was concentrated to one quarter volume in vacuo and diluted with water (25 ml). This process was repeated twice then evaporated to dryness in vacuo. The residue was dissolved in water and lyophilised to give an off-white solid (111 mg).

Intermediate 1B

Preparation of S-Benzyl-2-fluorothioacetimidate hydrobromide

Fluorothioacetamide (3.39 g) and benzyl bromide (6.23 g) were refluxed in chloroform (40 ml), under nitrogen, for 16 h. After colling, the mixture was diluted with ether (200 ml) and the resulting orange solid filtered off. The solid was washed with more ether and dried over $P_2O_5$ in vacuo to give 5.19 g of the desired product.

The following intermediates were prepared by an analogous method:

| | Intermediate Name | Mpt./° C. |
|---|---|---|
| 2B | S-benzyl 2-methoxylthioacetimidate hydrobromide from 2-methoxythioacetamide. | 140 |
| 3B | S-benzyl 2-benzyloxylthioacetimidate hydrobromide from 2-benzyloxythioacetamide. | 148–149 (dec) |

-continued

| | Intermediate Name | Mpt./° C. |
|---|---|---|
| 5B | S-benzyl 2-methylthiothioacetimidate hydrobromide from 2-methylthiothioacetamide. | 163–165 (dec) |

Intermediate C

Preparation of S-benzylthioacetimidate hydrochloride (intermediate)

A mixture of thioacetamide (15.0 g, 0.20 mol) and benzyl chloride (25.3 g, 0.20 mol) in chloroform (75 ml) was heated under reflux for 90 minutes (the thioacetamide required ~40 minutes to go into solution). The reaction mixture was then allowed to cool to room temperature and was then stood at 0° C. overnight, when colourless crystals formed as a layer on the surface. The product was filtered off, washed with cold 10% ether-chloroform and sucked dry to give the title compound (25.55 g) as colourless prisms. Mpt.=161°–163° C.

The hydrobromide salt was made by an analagous method in 85% yield; mpt=184°–186° C. dec.

EXAMPLE 1

Preparation of 2-Amino-6-(1-imino-2-fluoroethylamino)-4,4-dioxo-4-thiahexanoic acid dihydrobromide (a) t-Butyl-2-t-butoxycarbonylamino-6-(1-imino-2-fluoroethylamino)-4,4-dioxo-4-thiahexanoic acid hydrobromide To Intermediate A (609 mg) in ethanol (10 ml) at 0° C. was added Intermediate 1B (407 mg) in one portion. The mixture was stirred at 0° C. for 1 h, then at room temperature for 2 h. The solvent was removed in vacuo and the residue partitioned between water and ether. The aqueous layer was washed twice more with ether, then concentrated in vacuo. The residual gum was purified by column chromatography on silica, eluting with dichloromethane-methanol (8:1), giving a colourless foam (317 mg).

(b) 2-Amino-6-(1-imino-2-fluoroethylamino)-4,4-dioxo-4-thiahexanoic acid dihydrobromide t-Butyl-2-t-butoxycarbonylamino-6-(1-imino-2-fluoroethylamino)-4,4-dioxo-4-thiahexanoic acid hydrobromide (300 mg) was dissolved in glacial acetic acid (4.5 ml), and cooled whilst HBr in acetic acid (45% w/v, 1.5 ml) was added. The mixture was then stirred at room temperature for 2 h. The volatile materials were evaporated in vacuo and the residue dissolved in water. The solution was evaporated to dryness in vacuo, and this process repeated twice more. Ethanol was added to the residue and the mixture concentrated in vacuo to an off-white foam. The material could be further purified by dissolving in a minimum of warm ethanol and precipitating the product with ether to yield a white hygroscopic solid (220 mg) as the dihydrate.

The following compounds were prepared by analagous methods:

| Example No. | Compound Name | Mpt./° C. |
|---|---|---|
| 2 | 2-Amino-6-(1-imino-2-methoxyethylamino)-4,4-dioxo-4-thiohexanoic acid dihydrobromide dihydrate prepared from intermediates A and 2B. NMR ($D_2O$) δ 3.48(3H, s), 3.77–4.14(6H, m), 4.39(2H, s), 4.53(1H, d). | Glossy resin |

-continued

| Example No. | Compound Name | Mpt./° C. |
|---|---|---|
| 3 | 2-Amino-5-(2-acetoxy-1-iminoethylamino)4,4-dioxo-4-thiohexanoic acid dihydrobromide prepared from Intermediates A and 3B | |

EXAMPLE 4

Preparation of 2-Amino-6-(2-benzyloxy-2-iminoethylamino)-4,4-dioxo-4-thiahexanoic acid 1.67 hydrochloride 0.33 hydrobromide t-Butyl-6-(2-benzyloxy-1-iminoethylamino)2-t-butoxycarbonylamino-4,4-dioxo-4-thiahexanoate hydrobromide (0.97 g) (prepared by a method analagous to that described in Example 1A from Intermediates A and 3B) was stirred in 4M HCl/dioxane (12 ml) at room temperature for 6 hours. The solvent was evaporated and the residual gum triturated with dry ether (20 ml). A white solid slowly formed on standing. The ether was decanted off and the very hygroscopic solid washed with fresh ether and dried in vacuo with warming to 65° C.

The following compound was prepared by an analogous method:

| Example No. | Compound Name | Mpt./° C. |
|---|---|---|
| 5 | 2-Amino-6-(2-methylthio-1-imioethylamino)-4,4-dioxo-4-thiohexanoic acid prepared from Intermediates A and 5B | |

EXAMPLE 6

Preparation of 2-Amino-6-(2-hydroxy-1-iminoethylamino)-4,4-dioxo-4-thiahexanoic acid 1.67 hydrochloride 0.33 hydrobromide Example 4 (350 mg, 0.81 mmol) in a mixture of ethanol (15 ml) and water (5 ml) was hydrogenated at room temperature and atmospheric pressure over 5% palladium on carbon (Degussa type E101 NO/W, 80 mg) for 18 hours. The catalyst was filtered off and washed with water. The hydrogenation was then repeated using fresh catalyst (100 mg), for a further 18 hours. The catalyst was filtered off and washed with water, and the solvents evaporated. The residual gum was triturated with a small quantity of ethanol, resulting in the slow formation of a pale yellow solid. The ethanol was removed, and the very hygroscopic solid dried in vacuo at room temperature. Yield 240 mg.

EXAMPLE 7

Preparation of 2-Amino-6-(1-iminoethylamino)-4,4-dioxo-4-thiahexanoic acid

Method A (a) S-[2-(1-Iminoethyl amino) ethyl]cysteine

S-(2-aminoethyl)cysteine hydrobromide (12.25 g, 50 mmol) was dissolved in warm water (50 ml) and treated with basic copper carbonate (5.85 g). The solution was cooled, and filtered through Hyflo, and the residue was washed with water.

The blue solution of the copper protected cysteine derivative was stirred and cooled to 10° C. The pH was adjusted to 10 to 11 by the addition of 2N sodium hydroxide during which ethylacetimidate hydrochloride (9.375 g, 75 mmol) was added portionwise. The temperature was allowed to rise to room temperature and the solution adjusted to a pH of 3 by the addition of 2N hydrochloric acid. The solution was applied to a Dowex AG50WX8 column (100 ml bed volume), washed with water, and eluted with 0.2N Ammonia solution. The ninhydrin positive fractions were collected and the ammonia solution removed by evaporation in vacuo. The remaining solution was adjusted to pH 4 by the addition of 2N Hydrochloric acid. The solution was evaporated to dryness on a rotary evaporator to give 3 g of S-[2-(1-Iminoethylamino)ethyl]cysteine hydrochloride which was dried in a vacuum dessicator.

(b) 2-Amino-6-(1-iminoethylamino)-4,4-dioxo-4-thiahexanoic acid

A solution of S-[2-(1-iminoethylamino)ethyl]cysteine (3.25 g, 10 mmol) in 1M perchloric acid (20 ml) was treated with 30% hydrogen peroxide solution (6.8 ml, 60 mmol) and 0.5M ammonium molybdate (1 ml). The temperature of the resulting reaction was maintained at 30° C. by water cooling. The reaction mixture was stirred at 25° C. for 2 hours, after which time it was put on an AG 1X8 (acetate) ion exchange column (50 ml, 60 mmol). The amino acid was eluted from the column with water and the solvent was evaporated from the ninhydrin positive fractions to yield an oil. The oil was treated with ethanol and reevaporated in vacuo. The residual oil (approximately 4 g) was purified by flash column chromatography using methanol/ammonia (9:1) as the eluant to yield 0.8 g 2-Amino-6-(1-iminoethylamino)-4,4-dioxo-4-thiahexanoic acid.

Method B (a) S-(2-benzyloxycarbonylaminoethyl)cysteine sulphate

Liquid ammonia (6 L) was stirred in the reactor and L-cystine (300 g, 1.25 mol) was added carefully. The reaction mixture was stirred for 1 hour. Sodium (115 g, 5 mol) was added a piece at a time over 2 hours. A grey solution was formed. 2-(benzyloxycarbonylamino)ethane phenyl sulphonate (836 g, 2.5 mol) was added portionwise over 15 mins. The reaction mixture was stirred with ammonia under reflux overnight. The ammonia was allowed to evaporate off by switching off the circulation. The reaction was left overnight, then 9 liters of water was added, and the reaction warmed to 40° C. while stirring. The reaction mixture was cooled to room temperature and filtered. The filtrate was neutralised with dilute sulphuric acid. A white/yellow solid was removed by filtration and dried in a vacuum oven at 80° C. 715 g of the title compound was obtained. Mpt.=220°–221.5° C.

(b) S-(2-benzyloxycarbonyl-amino ethyl)-N-butyloxycarbonylcysteine

Butyloxycarbonyl anhydride (24 g, 0.11 mol) was added in 3 portions over 1½ hours to a stirred and ice cooled suspension of finely ground S-(2-benzyloxycarbonylamino ethyl)cysteine sulphate (39.5 g, 0.1 mol) in dioxane (400 ml) and water (200 ml) adjusting the pH to 9.5 with the addition of approximately 200 ml 1M sodium hydroxide. The dioxane was removed in vacuo and ethyl acetate added to the aqueous solution. The aqueous layer was adjusted to pH 2.8 by the addition of aqueous sulphuric acid and filtered. The filtrate was extracted with ethyl acetate. The ethyl acetate extracts were combined, washed with water and brine, dried over sodium sulphate and filtered. The solvent was evaporated in vacuo to give 42.95 g of the title compound.

(c) S-(2-benzyloxycarbonylamino)-N-butyloxycarbonylcysteine tert-butyl ester

A solution of S-(2-benzyloxycarbonyl-aminoethyl)-N-butyloxycarbonyl cysteine (3.98 g, 10 mmol) in dry benzene (15 ml) as heated to reflux and a little benzene distilled off to remove last traces of moisture. To the above solution at reflux was added dropwise over 20 minutes N,N-dimethylformamide di-tert butyl acetal (8.2 g, 40 mmol). The reaction mixture was then heated under reflux for 30 minutes until no further change was observed by tlc. The reaction mixture was cooled to room temperature, treated with water (15 ml) and stirred. The phases were separated out and the organic layer washed with 10% $KHCO_3$ (3×10 ml) and brine (2×10 ml). The aqueous phases were washed with fresh ether-benzene (1:1) (2×15 ml) and the 4combined extracts dried over $Na_2SO_4$, treated with charcoal, filtered and evaporated to dryness to give a pale tan oil. The crude material was purified by flash chromatography over $SiO_2$ using 65% cyclohexane-ethyl acetate as the eluant. 2.56 g of the title product was obtained as an almost colourless oil.

(d) 2-(butyloxycarbonylamino)-6-(benzyloxycarbonylamino)-4,4-dioxo-4-thiahexanoic acid tert-butyl ester To S-(2-benzyloxycarbonylamino)-N-butyloxycarbonylcysteine tert-butyl ester (454 mg, 1.0 mmol) in methanol (5 ml) at 0° C. was added dropwise a solution of "Oxone" (925 mg, 3.0 mmol) in water (5 ml) over 10 minutes. Throughout the addition, an exotherm was observed and the temperature was kept below 2° C. with external ice cooling. The reaction mixture was stirred at 0° C. for 4 hrs and then the allowed to warm to 15° C. over 10 hrs. Due to the reaction mixture being very viscous, additional aliquots of methanol (4 ml) and water (2 ml) were added to facilitate stirring. A further portion of "Oxone" (308 mg, 1.0 mmol) in water (1.5 ml) was added and the mixture stirred for a further 14 hrs. at room temperature. The reaction mixture was then treated with ether (3×25 ml) and the ethereal solution run off from the solid residue each time. The combined ethereal extracts were dried over $Na_2SO_4$, filtered and evaporated to dryness to give 0.428 g of the title compound as a colourless oil that rapidly solidified to a white solid. Mpt.=116°–118° C.

(e) 2-(butyloxycarbonylamino)-6-amino-4,4-dioxo-4-thiahexanoic acid tert-butyl ester To a solution of 2-(butyloxycarbonylamino)-6-(benzyloxycarbonylamino)-4,4-dioxo-4-thiahexanoic acid tert-butyl ester (200 mg) in methanol (5 ml) was added Pd/C (50%) (Degussa type) (200 mg) and the mixture hydrogenated at room temperature until no further change was observed. The reaction mixture was then filtered through a pad of Hyflo and the residue washed with fresh methanol (2×2 ml). The combined filtrates were evaporated to dryness to give 119 mg of the title compound as an almost colourless glass.

(f) 2-(butyloxycarbonylamino)-6-(1-iminoethylamino)-4,4-dioxo-4-thiahexanoic acid tert-butyl ester hydrochloride To a solution of 2-butyloxycarbonylamino)-6-amino-4,4-dioxo-4-thiahexanoic acid tert-butyl ester (340 mg) in methanol (10 ml) was added portionwise Intermediate C (202 mg). After stirring at 0° C. for 30 minutes, the reaction mixture was allowed to warm to room temperature and then evaporated to dryness. The oily residue was treated with water (2 ml) and extracted with ether (4×4 ml) to remove the benzyl mercaptan. The organic extracts were washed with fresh water (2 ml) and the combined extracts evaporated in vacuo at 40° C. to give 396 mg of the title compound as a colourless glass.

(g) 2-Amino-6-(1-iminoethylamino)-4,4-dioxo-4-thiahexanoic acid dihydrochloride

To a solution of 2-(butyloxycarbonylamino)-6-(1-iminoethylamino)-4,4-dioxo-4-thiahexanoic acid tert-butyl ester hydrochloride (300 mg) in dioxane (15 ml) was added 4N HCl/dioxane (10 ml) and the mixture allowed to stand at room temperature for 24 hrs. The reaction mixture was then evaporated to dryness and the semi-solid residue treated with water (2 ml) and evaporated to give a colourless glass. The crude product was purified by flash chromatography on $SiO_2$ using $CH_3CN:CH_3CO_2H:H_2O$ (5:2:2) as the eluant to give 172.5 mg of the title compound.

EXAMPLE 8

Preparation of 2-Amino-6-(1-iminoethylamino)-4-oxo-4-thiahexanoic acid

Method A (a) S-[2-(Iminoethylamino) ethyl]cysteine

S-[2-(Iminoethylamino)ethyl]cysteine (3 g, 0.0113 mol) was prepared according to the method described in Example 7, method A, step (a) above.

(b) 2-Amino-6-(1-iminoethylamino)-4-oxo-4-thiahexanoic acid

A solution of S-[2-(Iminoethylamino)ethyl]cysteine (3 g, 0.0113 mol) in 1M Hydrochloride acid (30 ml) was stirred, and then treated with 30% Hydrogen peroxide solution (1.5 ml 11.6 mmol). The reaction mixture was left overnight, after which time the reaction was shown to be complete by thin layer chromatography. The reaction mixture was put on an AG50WX8 column, washed with water and eluted with 0.5M ammonia solution. The ninhydrin positive fractions were collected and the solvent evaporated in vacuo. The crude product was purified by flash column chromatography using methanol/ammonia (9:1) as the eluant to yield 200 mg of 2-Amino-6-(1-iminoethylamino)-4-oxo-4-thiahexanoic acid.

Method B (a) 2-(butyloxycarbonylamino)-6-(benzyloxycarbonylamino)-4-oxo-4-thiahexanoic acid tert-butyl ester To a solution of S-(2-benzyloxycarbonylamino)-N-butyloxycarbonylcysteine tert-butyl ester (454 mg, 1.0 mmol), (prepared as described in Example 7, Method B, steps (a) to (c)), in dichloromethane (25 ml) at −2° C. was added m-chloroperbenzoic acid (426 mg @85% ≡2.10 mmol). A slight exotherm was observed, raising the temperature to +2° C. The reaction mixture was then stirred at 0° C. for 1½ hrs. After 1 hr the reaction was essentially complete. The reaction mixture was then extracted with 5% $KHCO_3$ (3×25 ml) and the organic layer dried over $Na_2SO_4$, filtered and evaporated to dryness to give a very pale tan oil. The crude compound was purified by flash chromatography on $SiO_2$ using 1.25% MeOH-EtOAc as the eluant to give 395 g of the title compound.

(b) 2-(butyloxycarbonylamino)-6-(benzyloxycarbonylamino)-4,4-dioxo-4-thiahexanoic acid tert-butyl ester The title compound was prepared by an analagous method to that described in Example 7, Method B, steps (e) to (g).

EXAMPLE 9

Biological Activity

The inhibition of purified human NO synthases was determined following preparation of human nNOS (Furfine et al. (1993) Biochem. 32, 8512–8517), iNOS (Sherman et al. (1993) Biochem. 32, 11600–11605) and eNOS (Garvey et al. (1994) Arch. Bioch. Biophys., in press) as described. Their activity was monitored by the conversion of [$^{14}$C]-L-arginine to citrulline as described by Schmidt et al. ((1991) Proc. Natl. Acad. Sci. USA 88, 365–369) in reaction mixtures (100 μl) containing 50 mM HEPES pH 7.0, 8 μM tetrahydrobiopterin, 1 mM NADPH and 0.5 μM [$^{14}$C]-L-arginine (30,000 cpm) at 30° C. The results are shown in Table 1 below.

TABLE 1

Inhibition of Purified Human NOS Isoenzymes

| Example No | Purified Human Enzyme $K_d$ (μM) iNOS | tNOS | nNOS | Selectivity for iNOS vs. cNOS [relative to LNMMA] |
|---|---|---|---|---|
| 1 | 1.9 | 23 | 26 | 12 [33] |
| 7 | 2.9* | 29 | 18 | 27 [73] |
| 8 | 9.1 | 100 | 68 | 11 [30] |

*This inhibition was strongly time dependant on iNOS; a $K_d$ value of 0.1 μm was determined suggesting an iNOS vs eNOS selectivity of 790 [>2000-fold greater than L-NMMA]

Inhibition of recombinant human iNOS was determined following expression in a baculovirus/insect cell system (Charles et al (1994) In: The Biology of Nitric Oxide 4, Moncada S., Feelisch M., Busse R. and Higgs E. A., eds., Portland Press, London, pp 316–320), assaying the insect cytosol for NO synthase in a microtitre plate assay based on the spectrophotometric assay described previously (Knowles et al (1990) Biochem. Biophys. Res. Commun. 172, 1042–1048). The assay was conducted at 37° C. in reaction mixtures containing HEPES (100 mM), DTT (0.1 mM), tetrahydrobiopterin (5 μM), NADPH (100 μM), haemoglobin (5 μM), L-arginine (30 μM) and inhibitor (0–300 μM), measuring the absorbance change at 405–420 nm, and determining the steady-state inhibition between 15 and 30 minutes incubation. The results are shown in Table 2 below.

The inhibition of eNOS and iNOS in situ in rat aortic rings was assessed by measuring the increases in ring tension caused by NO synthase inhibition. For studies of basal tone (reflecting eNOS), rings of thoracic aorta with intact endothelium were prepared as described previously (Rees et al. (1989) Br. J. Pharmacol. 96, 418–424) and cumulative concentration curves obtained for the inhibitors in the presence of a threshold concentration of phenylephrine ($ED_{10}$≈10 nM). For studies of induced smooth muscle tone (reflecting iNOS), endothelium-denuded rings were exposed to LPS (0.1 μg/ml from *S. typhosa*) in the presence of phenylephrine at approximately $ED_{90}$ for 6 h as described previously (Rees et al. (1990) Biochem. Biophys. Res. Commun. 173, 541–547). During this time a progressive loss of tone occurred because of iNOS induction. Cumulative concentration curves were then obtained for the inhibitors. The results are shown in Table 2 below.

| Example No. | $IC_{50}$ (μM) Recombinant Human iNOS | iNOS in rate sortic rings | cNOS in rat sortic rings | Selectivity for iNOS |
|---|---|---|---|---|
| 1 | 5.5 ± 0.55 (3) | 1.7 ± 0.7 (3) | >>300 (3) (8% inhibition at 300 μM) | >>200-fold |
| 2 | 30 ± 3 (3) | 33 ± 13 (3) | >300 (2) (26% inhihition at 300 μM) | >10-fold |
| 3 | >300 (3) | — | — | — |
| 4 | >300 (3) | — | — | — |
| 5 | 95 ± 3 (3) | — | — | — |
| 6 | >300 (3) | — | — | — |
| 7 | 14 ± 0.6 (3) | 1.5 ± 0.3 (6) | 101 ± 21 (6) | 67-fold |

-continued

| Example No. | $IC_{50}$ (μM) Recombinant Human iNOS | iNOS in rate sortic rings | cNOS in rat sortic rings | Selectivity for iNOS |
|---|---|---|---|---|
| 8 | — | 2.7 ± 0.2 (3) | 300 (2) (42% inhibition at 300 μM) | >100 fold |

The NO synthase efficacy and selectivity data are mean ±SEM from (n) experiments, or are mean ±SD if no brackets follows, from a single experiment.

The inhibition of eNOS and iNOS in vivo was assessed by the effects of inhibitors on blood pressure in either normal (eNOS) or endotoxin shocked (iNOS) conscious mice. Female CD-1 mice (25–35 g) were anaesthetised briefly with isofluorane (2%). Cannula lines were implanted in the femoral vein, tunnelled subcutaneously to exit at the top of the back and connected to a swivel tether system for continuous monitoring of blood pressure and for inhibitor administration respectively. Following recovery from surgery, animals with mean blood pressures in the normal range (90–110 mm Hg) were used to obtain cumulative concentration curves for inhibitors on blood pressure either without further treatment ("normal mice") or 7 h after administration of lipopolysaccharide (12.5 mg/kg of LPS from *E. coli* 026:B6 intravenously over 30 s) to induce shock ("shocked mice"). In normal mice Example 7 had no effect on blood pressure over the dose range 1–1000 mg/kg. However in shocked mice Example 7 was able to restore fully the blood pressure to the normal range.

The effects of Example 7 on endotoxin induced vascular leakage were assessed in rats as described by Laszlo et al ((1994) Brit. J. Pharmacol. 111 1309–1315). Example 7, at doses up to 5 mg/kg, when administered concurrently with endotoxin did not cause aggravation of the endotoxin-induced plasma leakage, unlike non-selective inhibitors such as L-NMMA. However, Example 7 did abolish the iNOS-dependent delayed plasma leakage, with an $ED_{50}$ of 1 mg/kg.

We claim:

1. A compound of formula (I)

(I)

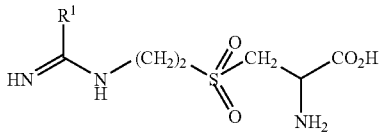

wherein $R^1$ methyl, [or fluoromethyl] or a salt, ester, amide or physiologically acceptable prodrug [thereof] *of said compound*.

[2. A compound of formula (I) according to claim 1 wherein the compound is selected from acid; and 2-amino-6-(1-imino-2-fluoroethylamino)-4,4-dioxo-4-thiahexanoic acid or a salt, ester, amide or physiologically acceptable prodrug thereof.]

[3. 2-amino-6-(1-iminoethylamino)-4,4-thiahexanoic acid.]

4. (R)-2-amino-6-(1-iminoethylamino)-4,4-dioxo-4-thiahexanoic acid.

5. A method for the treatment of a condition where there is an advantage in inhibiting NO production from arginine by the action of NO synthase, said method comprising administering to a mammal in need thereof a pharmaceutically effective amount of a compound of claim 1.

6. A method according to claim [4]*5* wherein the condition is a shock state resulting from overproduction of NO by iNOS.

7. A pharmaceutical formulation comprising a compound of claim 1, together with one or more pharmaceutically acceptable carriers therefor and optionally one or more other therapeutic ingredients.

8. A process of the preparation of a compound of claim 1 which comprises:

(a) oxidizing a compound of the formula (II):

(II)

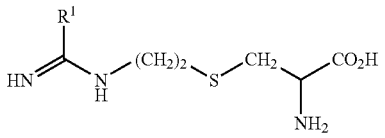

wherein $R^1$ is [as defined in claim 1]*methyl*, or (b) the deprotection of a compound of formula (V)

(V)

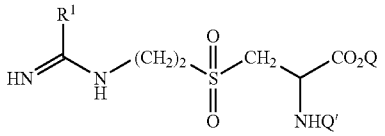

wherein $R^1$ [,] is [as defined above] *methyl*, Q is hydrogen or a carboxyl protecting group and Q' is a protecting group, *and* optionally [followed by] conversion into [another compound of formula (I)] *a salt, ester, amide or physiologically acceptable prodrug*.

9. An intermediate of formula (VI)

(VI)

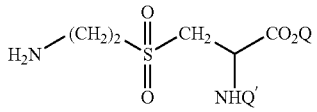

*excluding compounds* β-(β-*aminoethylsulphonyl*)-*N-toluene-p-sulphonyl-L-alanine and* β-(β-*aminoethylsulphonyl*)-*N-toluene-p-sulphonyl-L-alanine methyl ester hydrochloride,* or a protected derivative thereof, wherein Q and Q' are as defined in claim 8.

* * * * *

UNITED STATES PATENT AND TRADEMARK OFFICE

CERTIFICATE OF CORRECTION

PATENT NO. : RE 39,576 E
APPLICATION NO. : 10/407204
DATED : April 17, 2007
INVENTOR(S) : Hodson et al.

It is certified that error appears in the above-identified patent and that said Letters Patent is hereby corrected as shown below:

On The Title Page, Item (75) Inventors should read
--(75) Inventors: Harold Francis Hodson, Beckenham (GB); Richard Michael John Palmer, Hayes (GB); David Alan Sawyer, Beckenham (GB); Richard Graham Knowles, Stevenage (GB); Karl Witold Franzmann, London (GB); Barry George Shearer, Cary, NC (US);--

Item (56) Insert

--Foreign Patent Documents

| | | |
|---|---|---|
| DE | C 830 640 | 1/1952 |
| DE | A 43 10 202 | 10/1993 |
| EP | A 0 200 051 | 12/1986 |
| FR | 2 727 111 | *5/1996 |
| WO | WO A 93 13055 | 7/1993 |

UNITED STATES PATENT AND TRADEMARK OFFICE

CERTIFICATE OF CORRECTION

PATENT NO. : RE 39,576 E
APPLICATION NO. : 10/407204
DATED : April 17, 2007
INVENTOR(S) : Hodson et al.

It is certified that error appears in the above-identified patent and that said Letters Patent is hereby corrected as shown below:

Item (56) (cont'd)

*U.S. Patent Documents*

| | | |
|---|---|---|
| *5,945,408* | *8/1999* | *Webber et al* |
| *5,981,511* | *11/1999* | *Gapud et al* |
| *6,143,790* | *11/2000* | *Hallinan et al* |
| *6,207,708* | *3/2001* | *Gapud et al* |
| *6,576,780* | *6/2003* | *Gapud et al --* |

Signed and Sealed this

Seventh Day of August, 2007

JON W. DUDAS
*Director of the United States Patent and Trademark Office*